(12) United States Patent
Vemulapati et al.

(10) Patent No.: US 12,391,972 B2
(45) Date of Patent: Aug. 19, 2025

(54) CAPILLARY-BASED SYSTEM FOR ACCELERATED ANTIMICROBIAL SUSCEPTIBILITY TESTING

(71) Applicant: Cornell University, Ithaca, NY (US)

(72) Inventors: Sasank Vemulapati, Ithaca, NY (US); Ruisheng Wang, Ithaca, NY (US); David Erickson, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 588 days.

(21) Appl. No.: 17/132,496

(22) Filed: Dec. 23, 2020

(65) Prior Publication Data

US 2021/0189453 A1 Jun. 24, 2021

Related U.S. Application Data

(60) Provisional application No. 62/952,985, filed on Dec. 23, 2019.

(51) Int. Cl.
*C12Q 1/18* (2006.01)
*G01N 21/64* (2006.01)

(52) U.S. Cl.
CPC ........... *C12Q 1/18* (2013.01); *G01N 21/6408* (2013.01); *G01N 21/6428* (2013.01); *G01N 2021/6439* (2013.01)

(58) Field of Classification Search
CPC .. C12Q 1/18; G01N 21/6408; G01N 21/6428; G01N 2021/6439; G01N 2021/7766; G01N 2021/7786; G01N 21/78
See application file for complete search history.

(56) References Cited

U.S. PATENT DOCUMENTS

| | | | |
|---|---|---|---|
| 4,448,534 A | 5/1984 | Wertz et al. | |
| 5,164,301 A | 11/1992 | Thompson et al. | |
| 5,501,959 A | 3/1996 | Lancaster et al. | |
| 6,153,400 A | 11/2000 | Matsumura et al. | |
| 6,794,127 B1 | 9/2004 | Lafferty et al. | |
| 6,849,422 B1 | 2/2005 | Wiles et al. | |
| 7,642,068 B2 | 1/2010 | Steiner et al. | |
| 8,557,539 B2 | 10/2013 | Eden et al. | |
| 8,609,364 B2 | 12/2013 | Walsh et al. | |
| 8,828,680 B2 | 9/2014 | Williams et al. | |
| 9,012,209 B2 | 4/2015 | Eden et al. | |
| 9,850,457 B2 | 12/2017 | Sarver, Jr. et al. | |
| 10,161,948 B2 | 12/2018 | Vacic et al. | |
| 10,513,546 B2 | 12/2019 | Watters et al. | |
| 2013/0089876 A1* | 4/2013 | Sadik ................... | G01N 33/566 422/69 |
| 2017/0096631 A1 | 4/2017 | Uematsu et al. | |
| 2020/0149086 A1 | 5/2020 | Stern et al. | |
| 2020/0325518 A1 | 10/2020 | Spears et al. | |

FOREIGN PATENT DOCUMENTS

| | | | |
|---|---|---|---|
| CN | 106198471 A * | 12/2016 | ............. G01N 21/01 |
| WO | WO-2011031234 A1 * | 3/2011 | ............. B01L 7/525 |
| WO | 2019/201986 A1 | 10/2019 | |
| WO | 2020/073015 A1 | 4/2020 | |
| WO | 2020/109986 A1 | 6/2020 | |

OTHER PUBLICATIONS

CN 106198471 A. Dec. 7, 2016. Machine Translation. (Year: 2016).*

* cited by examiner

*Primary Examiner* — David W Berke-Schlessel
*Assistant Examiner* — Susan E. Fernandez
(74) *Attorney, Agent, or Firm* — Hodgson Russ LLP

(57) ABSTRACT

Provided are systems, devices, kits, and methods that are used for antimicrobial sensitivity testing (AST). The systems, devices, kits, and methods provide a capillary-based antimicrobial susceptibility testing platform referred to as "cAST" that provides faster determination of antimicrobial susceptibility using lower sample volumes than previous approaches. The cAST approach includes performing AST by measuring colorimetric or fluorescent signal changes in samples in conduits that contain antimicrobial agents and one or more dyes. The conduits are operably linked to a light source and a light detecting component through a mount configured to hold the conduits and thereby determine changes in light that indicates changes in bacteria growth in the present of the antimicrobial agents.

20 Claims, 5 Drawing Sheets

CAPILLARY-BASED SYSTEM FOR ACCELERATED ANTIMICROBIAL SUSCEPTIBILITY TESTING

CROSS REFERENCE TO RELATED APPLICATIONS

This application claims priority to U.S. provisional application No. 62/952,985, filed Dec. 23, 2019, the entire disclosure of which is incorporated herein by reference.

FIELD

The present disclosure relates generally to improved systems, devices and methods for analysis of bacteria, and response to antimicrobial agents.

BACKGROUND

In recent years, the emergence and increasing occurrence of antimicrobial resistant (AMR) microorganisms is a serious public health concern that places a substantial burden on the healthcare system. Infections due to these microorganisms are associated with longer hospital stays, poorer clinical outcomes, and increased healthcare costs[1]. The Centers for Disease Control and Prevention estimates that more than two million AMR infections occur in the United States each year, resulting in at least 23,000 deaths, $20 billion in excess direct healthcare costs, and $35 billion in lost productivity[2]. The threat of AMR is exacerbated by the over-prescription of broad spectrum antimicrobials as well as a paucity of new antimicrobials with novel mechanisms of action[1]. The empirical prescription of antimicrobials induces selective pressures that promote the development of AMR microorganisms. As a result, diagnostic methods that can eliminate diagnostic uncertainty and enable targeted treatment form one of the most effective ways to curb antimicrobial misuse and in turn the development of resistant microorganisms[3].

To facilitate the appropriate prescription of antimicrobials, common methods of assessing the antimicrobial susceptibility of bacterial isolates include broth dilution (in both manual and automated formats), and disk and gradient diffusion[4,5]. In broth dilution, bacterial inocula are cultured overnight in tubes of liquid growth medium supplemented with different antimicrobial concentrations. Following incubation, visual or optical inspection of the tubes for turbidity, which is evidence of bacterial growth, is conducted to determine the minimal inhibitory concentration (MIC). Quantitative determination of MIC is one of the primary advantages of broth dilution, but the technique is limited by its relative complexity and the need for overnight (16-24 h) incubation. In disk diffusion, bacterial inocula are cultured on an agar plate with paper disks, impregnated with antimicrobials, placed on the surface. Following an overnight incubation period, the zone of growth inhibition around each disk is measured. Disk diffusion has the advantages of being simple and low-cost but similar to broth dilution requires overnight incubation and is difficult to perform at the point-of-care[6]. In automated broth microdilution methods, incubation and optical detection systems are combined and used to detect bacterial growth in the presence of antimicrobials in a multi-well microdilution format, although manual preparation of inocula is typically required beforehand[6]. While automated instrumentation can be leveraged to simplify workflow and enable real-time measurements in some instances (although overnight incubation is often the norm), the high cost of the instruments and associated consumables limits their accessibility for use in point-of-care applications and resource-limited settings. Accessible antimicrobial susceptibility testing (AST) is crucial as evidence shows each hour delay in proper antimicrobial administration increases the risk of mortality in patients with severe sepsis[7,8].

Many alternatives to existing AST methodologies have been developed[9]. Examples of genotypic and phenotypic methods include tests based on antimicrobial resistance gene detection[10], microscopy[11,12], colorimetric detection[13,14], and microfluidics[15-18]. Because genotypic methods only determine the presence or absence of a resistance gene and thus antimicrobial susceptibility is inferred, phenotypic AST is needed to determine the antimicrobial susceptibility profile of an organism[19]. With phenotypic methods, speed of growth is fundamentally limited by the replication rate of the target organism; however, the analytic sensitivity of growth detection can be enhanced with the use of colorimetric indicators. For instance, resazurin, a redox indicator that undergoes irreversible color change in the presence of metabolically active bacterial organisms, has been shown to increase the analytic sensitivity of microbial growth detection compared to turbidity alone[20]. Despite the number of innovations in this area, the specialized training, instrumentation, and/or fabrication that many alternative AST techniques require have created barriers to adoption. Thus, there is an ongoing and unmet need for improved AST devices, systems and methods. The disclosure is pertinent to this need.

DESCRIPTION OF THE FIGURES

The concepts described herein are illustrated by way of example and not by way of limitation in the accompanying figures. For simplicity and clarity of illustration, elements illustrated in the figures are not necessarily drawn to scale.

(FIG. 1A) Realistic and non-limiting depiction of a cAST system comprising an incubator 10. During AST, capillary tubes 24 containing bacterial inocula are loaded into the cAST device 20, which is then placed inside a benchtop incubator 10. A fiber-optic cable 30 connects the cAST device 20 to an external spectrometer 40, which together with a microcontroller enables automated spectral intensity measurements. (FIG. 1B) The cAST device 20 is shown with exemplary dimensions of 8.2 cm by 10.2 cm by 7.6 cm, and is shown with fiber optic cable 30. (FIG. 1C) Exploded view of representative components of a system of the disclosure. The sample holder was designed to allow light from the LEDs to pass through the capillary tube 24 sample and into a fiber-optic detector. During data acquisition, the positioning of the fiber-optic cable 30 is controlled by the stepper motor 21 via rotation of the optical coupler 22. The cAST device 20 may comprise: a stepper motor 21; an optical coupler 22 connected to an output shaft of the stepper motor 21 at one end, and connected to the fiber optic cable 30 at the other end; a capillary mount 23 which receives a plurality of angularly arranged capillary tubes 24 in a capillary holder 35; and an LED holder 25, which may be substituted using any suitable light source.

(FIG. 2A) Comparison of detection of bacterial growth in capillary tubes and microwell using three colorimetric indicators: phenol red, bromomethyl blue, and resazurin. Bacterial metabolism induced color change in the media was tracked over time by measuring absorbance in the 350 nm-650 nm range. The difference in peak absorbance (peak wavelength shift) between a test sample and negative control sample (dye-supplemented media without bacteria) was used as a quantitative indicator of bacterial growth. Incubation inside capillary tubes with the dye resazurin was observed to yield the fastest time to growth detection. Error-bars denote one standard deviation (n=3). (FIG. 2B) Impact of capillary tube inner diameter size on time to growth detection. Inoculated media supplemented with resazurin was incubated inside capillary tubes with different inner diameters, denoted by $\Phi_1$, $\Phi_2$ and $\Phi_3$. Bacterial growth was tracked over time by measuring absorbance and determining peak wavelength shift relative to a negative control sample. Time to detection was determined as the time point at which a wavelength shift of greater than 25 nm was detected. An inversely proportional relationship was observed between capillary inner diameter and time to growth detection.

(FIG. 3A) Schematic of cAST setup illustrating use of resazurin as colorimetric indicator for phenotypic detection of bacterial growth. The cAST device 20 includes a plurality of conduits 24 illustrated by capillary tubes received in the mount 23. The mount 23 includes a plurality of capillary holders 35. The capillary tubes are shown to comprise a resistant culture sample 24a and a susceptible culture sample 24b. For resistant bacteria not inhibited by a particular antimicrobial concentration, subsequent proliferation over time leads to the reduction of resazurin into resorufin, which is characterized by a significant change in the color of the sample media. (FIG. 3B) Sample color change over time may be quantified through spectral measurement—either through measuring sample absorbance (using benchtop spectrophotometer) or through measuring the spectral intensity profile of light (using the portable spectrometer as part of the cAST platform) that passes through the sample. Changes in the peak absorbance/intensity wavelength of the sample relative to a negative control provide a quantitative indicator of bacterial growth. FIG. 3(C) shows a culture tube 50 used for storing culture samples. The culture tube 50 may comprise a tubular body 51 and a cap 52. FIG. 3D depicts a capillary tube 50 with exemplary dimensions of 17 mm by 100 mm. An advantage of sample incubation inside capillary tubes compared to other formats is that in a larger culture tubes, bacteria settle at the bottom as they grow and create an uneven growth environment. The relatively small inner diameter of the capillary, however, leads to a uniform distribution of bacteria within the sample matrix and maximizes access to nutrients which optimizes growth.

(FIG. 4A) Peak intensity wavelength shift over time for a kanamycin resistant E. coli strain (K12 ER2667). The difference in spectral peak intensity (wavelength shift) between a test sample and negative control sample provides a quantitative indicator of bacterial growth. The E. coli strain was tested with gentamicin (GEN) and kanamycin (KAN). For a non-inhibiting antimicrobial concentration, bacterial proliferation induced reduction of resazurin led to significant changes in the sample spectral intensity profile, as evidenced by drastic increases in peak wavelength shift. Error-bars denote one standard deviation (n=2). (FIG. 4B) Summarized AST results for five QC organisms: E. coli, E. cloacae, A. baumannii, P. aeruginosa, and a kanamycin resistant E. coli (K12 ER2667) strain. The markers denote the time at which wavelength shift exceeded a threshold, representing detection of organism growth. Numbers inside the markers denote antimicrobial concentrations in μg/mL. Gentamicin (GEN) is represented by a circular marker and kanamycin (KAN) is represented by a square marker. Individual wavelength shift data for each organism can be found in the supplementary materials. (FIG. 4C) AST results for two E. coli clinical isolates. Isolates were tested without prior knowledge of susceptibility profiles and cAST results were in categorical agreement with overnight clinical gradient diffusion results.

BRIEF SUMMARY

Figure 1:
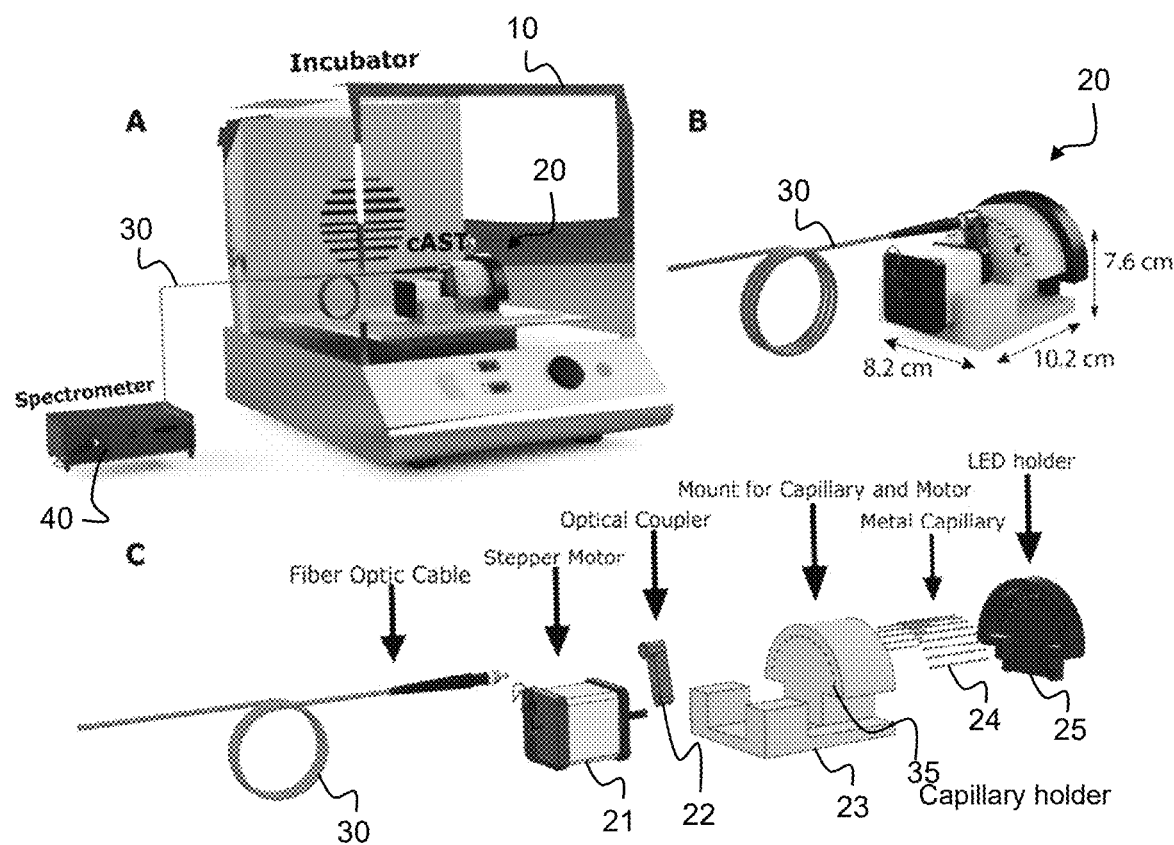
FIGS. 1A-1C. Overview of the cAST platform.

The disclosure provides devices, systems, kits, and methods that are used for determining AST. In embodiments, the disclosure provides a capillary-based antimicrobial susceptibility testing platform (referred to herein from time to time as "cAST") that provides accelerated assessment of antimicrobial susceptibility and lower sample volumes relative to previously available approaches. The disclosure demonstrates, among other attributes, that growth of bacteria using the described cAST approach is approximately 25% faster than in a conventional microplate. Results presented in this disclosure demonstrate the described cAST approach can provide accurate antimicrobial susceptibility test results within 4-8 h.

Non-limiting embodiments of a system of this disclosure is depicted in FIGS. 1A, 1B and 1C. Non-limiting embodiments of components of the described system are depicted in FIGS. 3A, 3C and 3D.

In embodiments, the disclosure provides a system configured to analyze antimicrobial susceptibility of bacteria. The system may comprise i) a mount defining at least one holder to receive a conduit (representative embodiments of which are shown using capillary tubes), which comprises a lumen configured to receive a liquid sample comprising bacteria. The sample contains or is modified to contain and a dye to measure bacterial growth. The described system comprises ii) a light source positioned or positionable at a first end of the conduit to output light along a longitudinal axis of the conduit. The system also comprises iii) a light detection device positioned or positionable at a second end of the conduit to receive light transmitted through the conduit by the light source. In certain embodiments, the conduit, or a plurality of conduits in the described system, are not transparent. In embodiments, the system includes a mount which comprises a plurality of holders configured to receive a corresponding plurality of conduits. Each conduit in the plurality of conduits is configured to receive a liquid sample comprising bacteria, a dye to determine bacterial growth, or both the bacteria and the dye to determine bacterial growth. In embodiments, the plurality of conduits are received within the holders and comprise a lumen having a diameter of 50 μm to 2 mm. In embodiments, the plurality of conduits are each 5-100 mm in length. In non-limiting embodiments the conduits comprise metal capillary tubes. In embodiments, the light source comprises one or more light emitting diodes (LEDs). In embodiments, the disclosure includes a light detection device to detect light that passes through a conduit and a sample. In embodiments, the light detection device comprises a spectrometer, or a photodiode and optical filter. A dye used in the described embodiments may be present in the plurality of conduits, and may comprise a redox sensitive dye, a non-limiting example of which comprises resazurin.

In embodiments, the conduits are at least substantially horizontally disposed to correspondingly maintain the conduits received therein in an at least substantially horizontal position. In embodiments, the described system and methods include a motor configured to move at least one of the light source or the light detection device between each of the plurality of conduits.

In another aspect, the disclosure provides methods for analyzing bacteria for antimicrobial susceptibility. The methods generally comprise i) introducing a liquid sample comprising or suspected of comprising bacteria into a first end of a conduit in a described system; ii) incubating the sample in the conduit in the presence of at least one antimicrobial agent; iii) transmitting light through a first end of the conduit using the light source; iv) detecting light emitted through a second end of the conduit using the light detection device to obtain an experimental value; and v) comparing the experimental value in iv) to a control value, wherein the comparison of the experimental value to the control value provides an indication of the sensitivity of the bacteria to the at least one antimicrobial agent. In embodiments, the control value comprises a value obtained from light detected using the light detection device from a liquid sample that comprises bacteria but does not comprise the antimicrobial agent. Alternative control values can be obtained and used by those skilled in the art when given the benefit of the present disclosure. In embodiments, the disclosure further provides for analyzing a plurality of liquid samples, wherein each liquid sample in the plurality of liquid samples is contained in a separate conduit, and wherein each of the liquid samples is equal to or less than 5 µL in volume, and wherein the indication of the sensitivity of the bacteria to the antimicrobial agent is obtained in not more than 8 hours. This approach provides for determining AST for a plurality of liquid samples, each of which contains a different antimicrobial agent.

In another aspect, the disclosure provides a kit for use in analyzing antimicrobial susceptibility of bacteria. The kit comprises at least one described conduit, and at least one of an antimicrobial agent, a bacteria culture media component, or an agent that produces a detectable signal when in the presence of growing bacteria. At least one of the antimicrobial agent, the bacteria culture media component, or the agent that produces the detectable signal, or a combination thereof, may be present within the conduit in the kit, such as in a dry form, which may be in contact with all or a portion of the surface of a lumen inside the conduit.

DESCRIPTION

Unless defined otherwise herein, all technical and scientific terms used in this disclosure have the same meaning as commonly understood by one of ordinary skill in the art to which this disclosure pertains. Every numerical range given throughout this specification includes its upper and lower values, as well as every narrower numerical range that falls within it, as if such narrower numerical ranges were all expressly written herein.

Ranges of values are disclosed herein. Unless otherwise stated, the ranges include all values to the magnitude of the smallest value (either lower limit value or upper limit value) and ranges between the values of the stated range. These include but are not limited to all values for bacterial detection, all time periods, temperatures, reagents, volumes, sizes (length, width, height, diameter, area), ratios, including but not limited to surface area to volume ratios, concentrations, methods of making the device(s) and system(s) described herein, and all methods of using the devices and system described herein. In embodiments, the disclosure comprises determining the presence or absence of bacteria, and may further comprise determining antibiotic sensitivity, including the presence or absence or such sensitivity.

In more detail, the present disclosure provides a novel capillary-based Antimicrobial Susceptibility Testing (referred to herein from time to time as "cAST") platform comprising components combined to enable phenotypic susceptibility testing in real-time. The provided platform includes an example mount or bracket (hereinafter "mount" 23), a non-limiting embodiment of which is shown in by the capillary mount 23 of FIG. 1C. Additional features of the described system are shown in the Figures and are described in Example 2. In embodiments, the mount may include a plurality of holders (e.g., openings, channels, receptacles, passages, through holes, clamps, or the like) in which conduits may be disposed, removably or non-removably, in a horizontal orientation, a substantially horizontal orientation, or a predominantly horizontal orientation. A representative capillary holder 35 is shown. The capillary holder 35 is dimensioned to receive conduit, illustrated using a metal capillary 24. The mount 23 may include a plurality of holders 35 in which a plurality of capillaries 24 may be disposed, and as also depicted in FIG. 3A. A capillary tube is a representative example of a conduit, as described herein. The conduit comprises a lumen, e.g., a channel that spans the length of the conduit.

The mount employs, in certain non-limiting embodiments, conduits, representative examples of which are shown as capillary tubes (e.g., metal capillary tubes), disposed within the holders in the mount, the conduits bearing therein a dye or marker (e.g., a resazurin dye, etc.), to enable accelerated detection of bacterial growth by means of spectral measurements of sample volumes that are significantly smaller than that needed to achieve reliable measurements in 96 or 384 well plates. The disclosure demonstrates that the cAST system can detect bacterial growth and determine AST data for clinically relevant organisms within 4-8 h of incubation. The example platform is an accessible alternative to conventional automated AST and is well-suited for use in resource-limited settings.

All systems, devices, and methods as depicted herein, including all components of such systems and steps of the methods, alone and in all possible combinations, are included in this disclosure. Non-limiting examples of devices and device components are depicted in the figures of this disclosure. Variations on the devices and components will be understood by those skilled in the art, given the benefit of this disclosure.

The disclosure includes all devices and systems described herein during operation. For example, a device described herein includes such a device with samples and/or bacteria present within one or more of its conduits, and further may include any one or combination of antimicrobial agents, such as antibiotics, against which bacteria within the device can be tested for resistance.

Any result obtained using the devices, systems and methods of this disclosure can be compared to any suitable reference, such as a known value, or a control sample or control value, suitable examples of which will be apparent to those skilled in the art, given the benefit of this disclosure.

The term "approximately" or "about" when used herein refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Any value given herein may also be limited to precisely the value stated.

Non-limiting examples of systems, devices, device components, and methods of the disclosure are illustrated by the accompanying figures.

In embodiments, the disclosure provides a device for analyzing bacteria, including but not necessarily for determining antimicrobial susceptibility (AST). In embodiments, a system and/or a device of this disclosure comprises one or more conduits for use in analysis of bacteria as further described below, a means of transmitting light into the conduits, and a means of detecting a signal emitted from the conduits. Further components may comprise a means of incubating bacteria (e.g., a benchtop incubator, etc.), a motor (e.g., a stepper motor, etc.), an optical coupler, a mount to hold one or more conduits and/or the motor and/or the optical coupler. A non-limiting depiction of a system/device of the disclosure is presented in FIG. 1. Further components may be provided and include a humidifying device, a heater, and/or a power source (e.g., a portable power source, such as one or more batteries). The device and/or any of its components may also be powered using conventional power supplies, including but not limited to standard outlets providing 120-240 volts.

Non-limiting embodiments of the disclosure are shown in the drawings, including FIG. 1A, FIG. 1B, FIG. 1C, FIG. 3A, FIG. 3C and FIG. 3D. FIG. 1A shows a representative cAST device 20. The cAST device may be positioned in or on an incubator 10. The cAST device 20 may be configured such that it is in communication with light detection device illustrated by a spectrometer 40, which may be positioned or positionable to receive the light. The cAST device may be connected in one or more locations to one or more fiber optic cables 30. FIG. 1B shows a non-limiting view of the cAST device 20 connected to the fiber optic cable 30. The cAST device 20 is shown with exemplary dimensions of 8.2 cm by 10.2 cm by 7.6 cm. FIG. 1C provides an exploded view of the cAST device 20 and the fiber optic cable 30. The cAST device 20 may comprise a motor illustrated by a stepper motor 21; an optical coupler 22 connected to an output shaft of the stepper motor 21 at one end, and connected to the fiber optic cable 30 at the other end. A representative mount 23 is configured to receive a plurality of angularly arranged conduits 24 illustrated by capillary tubes. A light source that is positioned or is positionable at a first end of the conduit 24 may be provided as a light emitting diode and that is held by a holder, the holder illustrated by a light emitting diode (LED) holder 25. The mount 23 comprises one or a plurality of conduit holders 35 which may comprise channels that run through the mount 23. FIG. 3A provides a detail view of the cAST device 20, wherein a plurality of conduits 24 shown as capillary tubes are received in the mount 23 via a plurality of conduit holders 35 which may comprises a resistant culture sample 24a and a susceptible culture sample 24b. FIG. 3C shows a culture tube 50 used for storing culture samples. The culture tube 50 comprises a tubular body 51 and a cap 52. The culture tube 50 is shown with exemplary dimensions of 17 mm by 100 mm. FIG. 3D shows a conduit 24 as a representative capillary tube.

The conduit 24 comprises a lumen 241 which extends the length of the capillary tube 24. The conduit 24 is shown with exemplary dimensions of 0.76 mm of internal diameter by 50 mm of length.

It will thus be recognized from the description and figures of this disclosure that conduits used in this device comprise an internal lumen that spans the length of the conduit. The conduits can be formed of any suitable material, non-limiting examples of which are described herein. In embodiments, the material does not allow light to pass through it. In embodiments, the material is not transparent. Thus, in embodiments, the material may be opaque. In embodiments, the material comprises a metal or other opaque material, such as a non-transparent plastic.

In embodiments, a transparent or translucent material is rendered non-transparent by, for example, coating the entire material, or an appropriate segment of the material, with an opaque substance, including but not limited to a paint, a film or a cladding. Thus, materials such as glass, quartz or silicon may be used, provided they are modified to be sufficiently opaque so as not to interfere with light transmission through an interior volume of the conduit, wherein said light transmission may be on a longitudinal axis, as further described below. In embodiments, a material used in, for example, a conduit 24 of this disclosure, may comprise or consist of a plastic. In embodiments, a lumen 241 of a conduit 24 of this disclosure may be partially or fully coated with a material. In embodiments, at least a portion of the lumen 241 may be coated with a substance which may include a compound that can facilitate production of a detectable signal, e.g., a dye, or may include an antimicrobial agent, or may include components of culture media that are intended to support bacterial growth. The described substances may thus be disposed on an internal surface of the conduit 24, e.g., on a surface in the lumen 241. The substance may be provided as, for example, a dry coating that is suitable for reconstitution once a liquid sample is introduced into the conduit. The sample may comprise bacteria and liquid culture media, or another liquid media that dissolves the substance to provide a culture media. The dye or other substance(s) are provided in a sufficient amount to yield a concentration in the liquid culture sample to perform any of the described assays. In embodiments, at least one of the described substances is provided as a component of the culture medium. In embodiments, an antimicrobial agent is provided in the conduit. The antimicrobial agent may be provided as a component of the dry coating that is suitable for reconstitution once a sample is introduced into the conduit.

The conduit 24 and its lumen 241 may comprise a first open end and a second open end, and may include only a first and second open end, e.g., no other openings are included. In embodiments, one open end of a conduit 24 comprises and inlet, and the other open end comprises an outlet.

In some examples, the conduit 24 comprises a closed end at a distal end of the conduit 24 and an open end at a proximal end of the conduit 24, wherein the closed end is transparent.

In some examples, the conduit 24 comprises a closed end or selectively closed end at a distal end of the conduit 24 and an open end at a proximal end of the conduit 24, wherein the closed end comprises a mirrored surface facing an interior volume of the conduit 24.

In some examples, the conduit comprises 24 a first removable cap to selectively occlude the first open end and a second removable cap to selectively occlude the second open end, wherein the first removable cap and the second removable cap are transparent at least in portions disposed adjacent to an interior volume of the conduit.

In embodiments, the conduit 24 and/or the lumen 241 comprises a cylindrical shape, such as a tube, but alternative shapes may be used, such as rectangular, triangular, or oval. In embodiments, the conduit is straight, but other shapes may also be used, including conduits comprising one or more curves or bends, such as in a serpentine shape, provided such non-straight configurations are able to transmit a light signal through the lumen of the conduit.

In embodiments, a plurality of conduits 24 are provided. A plurality of conduits 24 may comprise from 2-100, or more conduits. In embodiments, from 2-20 conduits are included. In embodiments, 2, 3, 4, 5, 6, 7, 8, 9, 10, 11, 12, 13, 14, 15, 16, 17, 18, 19, or 20 conduits are included. In one non-limiting embodiment, 15 conduits are included. In embodiments, an array of conduits are provided (e.g., an n×m array, an n×n array, where n may comprise any integer, inclusive of 1, and m may comprise any integer different than n).

The conduits may be arranged in any suitable manner. In some examples, one or more conduits may be dissimilar (e.g., different diameter, different length, different shape, etc.) from one or more other conduits. In embodiments, a plurality of conduits are substantially parallel to one another. In an embodiment, such as illustrated in FIG. 1, the conduits 24 may be provided in a curved or curvilinear array. In embodiments, the conduits may be configured to be disposed in a light path (e.g., proximal to or distal from) of a suitable light source so that the incident light enters into a first open end of the conduit and enters an interior volume of the conduit. The conduits may be configured such that light emitting from a second open end is in communication with a light detector, as further described below and illustrated in non-limiting embodiments in the figures. In some examples, a motor 21 is configured to position a light pipe, such as fiber optic cable 30, to receive light through the second open end of the conduits, and thus may move the light pipe accordingly. The light pipe may be in communication with any suitable light detector(s), non-limiting examples or which are described below. In some examples, a motor 21 is configured to position a light sensor to directly receive light through a second end (e.g., open end or closed end) of a plurality of conduits, and thus may move the light sensor accordingly.

In some examples, a light sensor 40 and a light source held in a light source holder 25 are both provided proximal to a first end of a conduit 24 and an emitted light from the light source is reflected from a closed second end of the conduit 24 to be incident to the light sensor 40.

In some examples, a dedicated light sensor is fixed relative to a second end (e.g., an open end or a closed end) of a specific conduit to receive light output from the second end of the specific conduit. In some examples, a light source is fixed relative to a first end (e.g., an open end or a closed end) of a specific conduit to emit light into the first end of the specific conduit. In some examples, a plurality of light sources and/or a plurality of light sensors are provided and motor is not required to correspondingly move the light source and/or the light sensor from a first conduit to a second conduit.

In some examples, the mount 22 defines the conduits 24 in which samples are to be disposed rather than defining holders 35 in which conduits 24 may be removably or non-removably disposed.

In embodiments, conduits used in devices/systems/methods of the disclosure have an internal lumen with a diameter of approximately 50 micrometers to 2 mm. In embodiments, the lumen has a diameter of 0.10 mm to 2.00 mm, inclusive, and including all numbers and ranges of numbers there between to the second decimal point. In embodiments, a conduit of the disclosure comprises a lumen with a diameter that is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.0 mm in diameter. In non-limiting embodiments, the conduits have an internal diameter of approximately 0.40 mm to 0.80 mm. In embodiments, the internal diameter of the lumen is approximately 0.45 mm, 0.70 mm or 0.76 mm. In an embodiment, an internal diameter of the lumen that is approximately 0.76 mm provides for preferable accelerated growth and optical signal intensity.

In embodiments, the conduits have any suitable length. In embodiments, the conduits are from approximately 5-100 mm in length, inclusive, and including all numbers and ranges of numbers there between. In embodiments, the conduits are approximately 5-50 mm in length. In embodiments, the conduits are approximately 50 nm in length.

In embodiments, one or more components of a device of this disclosure can be connected to or in communication with a digital processor and/or a computer running software to interpret a signal. A processor may also be included as a component of the device or system comprising the device, wherein the processor runs software or implements an algorithm to interpret an optically detectable signal, and may generate a machine and/or user readable output.

In embodiments, information obtained by the device/system can be monitored in real-time by a computer, and/or by a human operator. In certain embodiments, the disclosure provides as an embodiment or component of the system a non-transitory computer readable storage media for use in performing an algorithm to control signal generation and/or detection, and/or for monitoring and/or recording signaling events. In certain embodiments a device of this disclosure comprises microprocessor wherein the microprocessor is a component of an Arduino board. The device may further comprise a suitable Arduino WiFi shield and WiFi component in order to communicate with additional components. In embodiments, a system described herein may operate in a networked environment using logical connections to one or more remote computers. In embodiments, a result obtained using a device/system/method of this disclosure is fixed in a tangible medium of expression. The result may be communicated to, for example, a health care provider.

In embodiments, a device of this disclosure includes a light source. Any suitable light source can be used. A non-limiting embodiment comprises one or more light emitting diode (LED) lights. In embodiments, one or more fluorescent light sources may be used. In embodiments, distinct light sources are used for each of the conduits in a device described herein. In embodiments, the light source is positioned or positionable at a first end of a conduit to output light along a longitudinal axis of the conduit. In embodiments, the light source and/or, for example, a fiber optic cable in communication with the light source, can be moved sequentially such that it transmits light to individual conduits. In embodiments, a single light source, or a plurality of light sources, can be configured to transmit light into first ends of a plurality of conduits sequentially or concurrently. In embodiments, the light emitted by a light source is only transmitted along a substantially longitudinal axis of a conduit. In embodiments, the light and conduits may be configured, for example, so that light incident on one end of the conduit passes through a sample in an interior volume of the conduit and is captured by, for example, a light pipe such as a fiber-optic cable or an optical wave-guide. In embodiments, the light source is positioned such that light enters a first end of a conduit, and a signal detector is positioned to detect a light signal that exits a second end of the same conduit. Thus, in embodiments, conduits of this disclosure may exclude optically transparent windows that are disposed anywhere on the surface of the conduits. In embodiments, the conduits are not formed from PDMS. FIG. 1 provides a non-limiting depiction of components of an example system of the disclosure.

In embodiments, the light pipe (e.g., fiber optic cable or any suitable alternative) is disposed in communication with a light detection device. Thus, in embodiments, the disclosure provides for readout of a signal from conduit that is optically accessible, such as light that is emitted from an end of the conduit that is in communication with a light detection device.

In embodiments, the light detection device detects any one or a combination of light intensity, wavelength, optical density, fluorescence, and combinations thereof. Any suitable light detection device (e.g., a signal detector) can be used, examples of which include but are not limited to a spectrometer, spectrophotometer, a charge-coupled device (CCD) camera, a microscope, including but not limited to a fluorescent microscope, or a photodiode and optical filter configurable to detect the appropriate wavelength emitted from a dye, for example. In embodiments, a portable spectrometer may be included. Thus, in embodiments, the light detection device is positioned or positionable at a second end of the conduit to receive light transmitted through the conduit by the light source.

In embodiments, the disclosure provides for use of an agent that produces a detectable signal. In embodiments, the agent comprises a dye, which may be a fluorescent or non-fluorescent dye. In embodiments, the dye is pH sensitive, or pH insensitive. In embodiments, the dye is phenol red or bromomethyl blue. In embodiments, the agent that produces a detectible signal comprises a redox sensitive compound, such as basic fuchsin, methyl green, crystal violet, or methylene blue. In embodiments, the redox sensitive compound comprises a compound that results in a detectable change in a color in the sample. In embodiments, the redox sensitive agent results in a change of one color to another color in the tested sample. In embodiments, the redox sensitive agent results in a change of a colorless sample to a sample that exhibits color. In embodiments, the intensity of a color is changed. In embodiments, the disclosure includes use of a redox sensitive dye that is Resazurin (7-Hydroxy-3H-phenoxazin-3-one 10-oxide). In embodiments, the disclosure includes determining a change in a detectable signal that is produced at least in part by formation of a reductant. In embodiments, colorimetric and fluorescence signal detection may be used.

In embodiments, a change, such as an increase in optical density indicates bacteria cell death, such as that caused by an antimicrobial agent. In embodiments, a change in spectral intensity, absorbance, optical density, or fluorescence is indicative of bacterial proliferation, which in turn is indicative of non-susceptibility to a particular antimicrobial agent concentration.

In embodiments, a color change in, for example, a fluid, is determined by measuring a change in absorbance or spectral intensity. In embodiments, absorbance in a range of approximately 350 nm-650 nm is determined. A change in any light signal can be measured at a single or several time points.

In embodiments, a difference in peak absorbance (e.g., peak wavelength shift) between a test sample and negative control sample, such as a dye-supplemented media without bacteria, may be used as a quantitative indicator of bacterial growth.

In embodiments, light detection is performed at more than one time point over a period of time until a threshold wave-length shift is determined. In a non-limiting embodiment, a wave-length shift of greater than about 25 nm is a suitable threshold.

In embodiments, a color change over time is determined and may be quantified using spectral measurements. Thus, in embodiments, the disclosure employs use of resazurin or any suitable alternative dye as colorimetric and/or fluorescent indicator for phenotypic detection of bacterial growth. In embodiments, for resistant bacteria not inhibited by a particular antimicrobial compound and/or compound concentration, subsequent proliferation over time leads to the reduction of resazurin into resorufin, which is characterized by a significant change in the color of the sample media. A non-limiting demonstration of results from using this approach is shown in FIG. 3B.

In embodiments, a computer readable storage medium can be a component of a device of this disclosure, and can be used during or subsequent to performing any assay or one or more steps of any assay described herein. In embodiments the computer storage medium is a non-transitory medium, and thus can exclude signals, carrier waves, and other transitory signals.

In embodiments, a sample used in a device, system and/or method of this disclosure comprises any suitable biological sample that can comprise bacteria. In embodiments, a liquid biological sample is used. In embodiments, the liquid biological sample comprises blood, urine, lacrimal secretions, seminal fluid, cerebrospinal fluid, or any other biological fluid. In embodiments, the sample is used directly, or is subjected to a processing step prior to being analyzed using as described herein. In embodiments, a skin sample is processed into a liquid sample and is tested using the described methods. In embodiments, the sample tested is from a human, or a non-human animal, and is thus suitable for human and veterinary diagnostic purposes. In embodiments, a sample comprises a swab, or liquid sample obtained from any environment, surface, or device, or a sample of a biological tissue that it has been liquefied. In embodiments, the sample is obtained from an individual who has been diagnosed with, or is suspected of having, a bacterial infection. In embodiments, the bacterial infection comprises an infection of a tissue, including but not necessarily limited to skin, an infection of the gut, an infection of a urogenital tract, an infection of the ear, an infection of the eye, or an infection of the blood, which may or may not comprises sepsis.

In embodiments, the disclosure comprises a method comprising introducing a liquid biological sample into at least one conduit of a device as described herein, and identifying the presence or absence or amount of bacteria, and/or antibiotic sensitivity or resistance to one or more antibiotics, as further described herein. In embodiments, the sample volume introduced into the device is from 1 µl to 10 µl. Thus, in embodiments, the sample volume introduced into the device is approximately 1, 2, 3, 4, 5, 6, 7, 8, 9, or 10 µl. In embodiments, the sample volume is approximately 4 µl. In embodiments, the sample volume is less than approximately 5 µl and is more than 0.1 µl.

In embodiments, the sample is introduced into an open end of the conduit that is proximal to the light source.

In embodiments, a sample comprises approximately $1 \times 10^5$ CFU/mL-$1 \times 10^6$ CFU/mL, inclusive, and include all numbers and ranges of numbers there between, of bacteria. In embodiments, the sample comprises approximately $5 \times 10^5$ CFU/mL.

The bacteria in the sample may comprise any type of bacteria, and may include mixtures of distinct bacteria. The bacteria may comprise mixed populations of bacteria, which may include different strains of the same species of bacteria, and may also include more than one type of bacterial species. Gram positive and gram negative bacteria are include. In non-limiting embodiments, the bacteria in the sample may comprise any of *Streptococcus, Staphylococcus, Clostridium, Bacillus,* or *Salmonella,* including all species and strains of such bacteria. In embodiments, the bacteria include *Escherichia coli* (*E. coli*). In non-limiting embodiments, the disclosure provides for determining the presence or absence of methicillin-resistant *Staphylococcus aureus* (MRSA), vancomycin-resistant *S. aureus* (VRSA), extended spectrum beta-lactamase (ESBL), vancomycin-resistant Enterococcus (VRE), and/or multidrug-resistant *Acinetobacter baumannii* (MRAB). In embodiments, the disclosure provides for determining development of AST by measuring a series of samples over a period of time. The disclosure further comprises testing bacteria that have been identified as demonstrating antimicrobial resistance to determine one or more genes that contribute to said resistance. In embodiments, pathogenic bacteria are identified. In alternative embodiments, the described systems, devices, and methods may be adapted to determine antimicrobial resistance for pathogenic fungi, such as filamentous fungi that are known to cause infections in humans and non-human animals.

In embodiments, samples are introduced into one or more conduits 24 using only a force that comprises or consists of capillary flow. Thus, the use of, for example, pumps, mechanical or manually applied pressure, a vacuum, and the like, may be excluded from any device, system and method of this disclosure. Likewise, the use of oils, emulsions, and the like, to facilitate transport of the sample through the conduits may be excluded from the scope of this disclosure.

In embodiments, the disclosure provides for determining AST. AST analysis can be performed by, for example, exposing bacteria in conduits described herein to one or more antibacterial agents, such as an antibiotic, and determining whether or not the agent is lethal to the bacteria, or inhibits the growth of the bacteria. The type of antibiotic is not particularly limited. In embodiments, AST is determined for any of narrow-spectrum beta-lactam antibiotics of the penicillin class of antibiotics, or any other type of antibiotic, including but not limited to antimicrobial peptides. In embodiments the antimicrobial agent comprises an antibiotic that is any type of penicillin, cephalosporin, tetracycline, or aminoglycoside. In embodiments, the antibiotic is any of a carbapenems, fluoroquinolone, a macrolide, a monobactam, or an oxazolidinone. In specific and non-limiting embodiments, the antibiotic comprises kanamycin, gentamicin, methicillin, vancomycin, fidaxomicin or metronidazole.

A plurality of distinct antimicrobial agents can be tested. Only one, or more than one antibiotic can be tested in each conduit. In embodiments, single, distinct antibiotic agents are tested separately in separate conduits, e.g., a plurality of conduits. In embodiments, distinct concentrations of the same antibiotic are tested. In embodiments, distinct concentrations of a plurality of antibiotics are tested. In embodiments, bacteria analyzed using the described systems, devices, and methods may be determined to be not resistant to any antibiotic, resistant to only one antibiotic, or to be resistant to more than one type of antibiotic, thereby exhibiting multi-drug resistance. In embodiments, the bacteria may be determined to be extensively drug resistant (XDR) or totally drug-resistant (TDR).

In embodiments, the disclosure comprises screening test agents to determine whether or not they may be candidates for use as antibiotics.

In embodiments, AST testing of bacteria is complete within a period, subsequent to introducing the bacteria containing sample into the conduits, of approximately 1-24 hours, inclusive, and including all time periods in minutes and ranges of minutes there between. In embodiments, AST testing is performed in a period of not more than about 8 hours. In embodiments, AST testing is completed in a period of from about 4-8 hours. In embodiments, AST testing is completed in a period of not more than 8, 7, 6, 5, or 4 hours, inclusive, and including all time periods in minutes and ranges of minutes there between. Each of the described time periods may comprise a bacteria incubation period.

In embodiments, growth of bacteria in conduits described herein is faster than in a control. In embodiments, the control comprises a conventional microplate well. In embodiments, a conventional microplate well volume is about 75-700 µL. In embodiments, a conventional microplate well volume is about 360 µL. In embodiments, a conventional microplate well has a working volume of about 75-200 µL. In embodiments, growth of bacteria in a conduit of this disclosure is about 25% faster than growth in a conventional microplate well.

In embodiments, the disclosure provides for testing a sample obtained from an individual to develop a treatment and/or treatment recommendation for the individual. For example, a sample can be obtained from an individual who is suspected of having or is known to have a bacterial infection. The sample may be processed using a device/system/method of this disclosure to assess the sensitivity of bacteria in the sample to one or a plurality of antibiotics. In the case where the bacteria are not resistant to a particular antibiotic, the device may accordingly aid in a physician or other health care provider recommending treatment with the antibiotic to which the bacteria are not resistant. Alternatively, the sample may be determined to comprise bacteria that are resistant to one or more antibiotics, but are sensitive to one or more different antibiotics. This aids in a physician or other health care provider recommending treatment of the individual from whom the sample was obtained with the one or more antibiotics to which bacteria in the sample are not resistant. The disclosure further comprises administering said antibiotic(s) to the individual. In embodiments, the disclosure provides for monitoring an individual for the presence or absence of antimicrobial resistant bacteria. In an embodiment, and individual is diagnosed with an infection comprising antimicrobial resistant bacteria, the individual is then treated with an antibiotic to which the bacteria are determined, such as according to the disclosure, to be sensitive, and one or more subsequent samples from the individual are tested according to the disclosure to determine whether or not the antimicrobial resistant bacteria are reduced or eliminated from the individual.

In embodiments, the disclosure comprises a kit. The kit may comprise conduits described herein, which may be provided alone, or as a component of a cartridge or similar component. The conduits may be provided pre-loaded with any combination of antibiotics, one or more dyes, and bacterial culture media/nutrients. Such components may be provided within the conduits in dry form, such as a lyophilized form, for reconstitution when a sample is loaded into the conduit(s).

The following examples are intended to illustrate but not limit the disclosure.

EXAMPLE 1

The following materials and methods were used to produce the results described in the subsequent Examples.

Comparison of Growth in Capillary Versus Microwell Format

To examine the impact of incubation format on bacterial growth in small volumes, bacterial incubation in capillary tubes was compared to incubation in wells of a 384-microwell plate. Using the same dilution steps described in the susceptibility testing section, an overnight culture of *Escherichia coli* ATCC 25922 was diluted to a starting concentration of ~$5 \times 10^5$ colony-forming units per milliliter (CFU/mL) in Cation-Adjusted Mueller-Hinton Broth (CAMHB, Becton, Dickinson and Company) and supplemented with 10% v/v of three different colorimetric indicators separately: phenol red (MilliporeSigma), bromomethyl blue (MilliporeSigma), and resazurin (PrestoBlue, Thermo Fisher). For all three colorimetric indicators, metabolically active bacteria induce color change in the media over time, which can be quantified through measuring sample absorbance. By testing three colorimetric indicators and two sample incubation formats, we determined which combination yields the fastest detection of growth. A defined volume, 15 μL, of each dye-supplemented culture was loaded into multiple capillary tubes of size 65 mm×0.97 mm×0.70 mm (length [L]×outer diameter [O.D.]×inner diameter [I.D.], Drummond Scientific) via capillary action and wells of a 384-microwell plate (VWR) via pipetting. The 15 μL volume was selected to facilitate even coating of the well bottoms for consistent absorbance measurements. Loaded capillary tubes and the master microwell plate were incubated at 37° C. in ambient air. Sample absorbance in the 350 nm to 650 nm range with 1 nm resolution was measured using a SpectraMax Plus 384 microplate reader at the following time points: 0, 60, 90, 120, 135, 150, 165, 180, 195, 210, 225 and 240 min. For absorbance measurements, capillary and microwell samples containing each of the three colorimetric indicators were transferred to a new 384-microwell plate in duplicate along with dye-supplemented CAMHB without bacteria as negative control. The difference in peak absorbance (peak shift) between a test sample and negative control sample was used as a quantitative indicator of bacterial growth. In a separate experiment, bacterial growth inside capillary tubes with different inner diameters (0.45 mm, 0.70 mm, and 0.76 mm) was quantified using the same spectroscopic approach.

cAST Platform Design and Operation

A non-limiting embodiment of a system of the disclosure, e.g., the cAST platform, may contain the following components which are also discussed above in connection with the figures: custom motor mount/sample holder, optical coupler, light emitting diode (LED) holder as light source, a stepper motor, microcontroller, capillary tubes as the conduits, and portable spectrometer as a light detection device. Custom device parts were designed in SolidWorks (Dassault Systemes) and 3D printed using an Objet 3D printer. The motor mount/sample holder houses a bipolar stepper motor (Spark-Fun Electronics) that drives the optical coupler during data acquisition as well as 1/16 in. stainless steel capillary tubes (Supelco) that hold the samples. The optical coupler enabled precise alignment of a 400 μm fiber-optic patch cable (Edmund Optics) with the capillary tubes. The patch cable was connected to a portable spectrometer (Ocean Optics HR2000) that was used for spectral intensity measurements of samples. The LED holder was fixed with 10 high-power white LEDs (Lite-On, Inc.) that served as the light-source for measurements. A transistor array was soldered to the stepper motor to allow for precise control of the motor spindle. An Arduino Uno microcontroller was connected to the transistor array and LEDs and programmed to automate spectral intensity measurement of the capillary tubes following a fixed time interval.

The disclosure includes use of steel capillary tubes of size 50 mm×1.59 mm×0.76 mm (L×O.D.×I.D.) to hold the samples. Alternatively, glass capillary tubes (Drummond Scientific) of similar size can also be used. However, in the case of glass, the ends of the tubes are coated with paint or a similar substance to prevent excess light from the LEDs leaking into the fiber-optic detector. During sample loading, 4 μL liquid culture droplets were individually pipetted onto a clean substrate and then loaded into the tubes via capillary action. The capillary tubes used as conduits were sterilized prior to loading through autoclaving. Following loading, tubes were inserted into the sample holder in a configuration that allows light from the LEDs to pass through the sample and into the fiber-optic detector. Since the volume capacity of the capillary tubes was higher than the sample volume of 4 μL, the tubes were loaded with the fluid-filled side near the light-source as this configuration was determined to yield higher signal-to-noise ratios. This approach to sample loading is encompassed by the disclosure. During AST, the cAST platform was placed inside a benchtop incubator (Corning) set to 37° C. in ambient air. A small portable humidifier was also placed inside the incubator (80-85% relative humidity) to minimize sample drying during incubation. Thus, in embodiments, a system of the disclosure may include a humidifying device or composition to act as a desiccant. Every 30 min, spectral intensity measurements were automatically taken for each sample and data were transferred and stored on a computer for processing using OceanView (Ocean Optics).

Antimicrobial Susceptibility Testing Using the cAST Platform

The cAST platform was initially used to test five different quality control (QC) strains: *Escherichia coli* ATCC 25922, *Enterobacter cloacae* ATCC 13047, *Acinetobacter baumannii* ATCC BAA-747, *Pseudomonas aeruginosa* ATCC 27853, and *Escherichia coli* K12 ER2267 (kanamycin resistant). To prepare inocula for AST, strains were first streaked on Mueller-Hinton II agar plates (Becton, Dickinson and Company) and incubated overnight at 37° C. in ambient air. For the kanamycin resistant *E. coli* K12 strain, the agar was supplemented with kanamycin (MilliporeSigma) at a final concentration of 50 μg/mL. Liquid cultures were then prepared by inoculating single colonies into CAMHB, followed by overnight incubation at 37° C. in ambient air. To achieve the recommended starting inoculum concentration of $5 \times 10^5$ CFU/mL[21], the overnight culture was adjusted using CAMHB to the equivalent turbidity of a 0.5 McFarland standard, which represents a concentration of approximately $1 \times 10^8$ CFU/mL. Using a spectrophotometer (V-1200, VWR), the OD625nm absorbance corresponding to a 0.5 McFarland standard was verified to be in the range of 0.08-0.13[21]. The 0.5 McFarland suspension of bacterial organism was diluted 1:100 in CAMHB media, split into subcultures, and supplemented with varying concentrations of antimicrobials and a resazurin (PrestoBlue, Thermo Fisher) solution (10% v/v final concentration) to achieve an approximate starting inoculum concentration of $5 \times 10^5$ CFU/mL. Resazurin is a redox indicator that is reduced by metabolically active cells into resorufin, leading to significant colorimetric and fluorescent changes in the culture media which can be measured to gauge bacterial growth[20]. The aminoglycoside gentamicin was selected to be the target antimicrobial for susceptibility testing since it is classified by the Clinical and Laboratory Standards Institute (CLSI) as a Group A (appropriate for inclusion in primary AST panel) antimicrobial agent for the organisms used in this study[22]. The *E. coli* K12 kanamycin resistant strain was additionally tested with kanamycin. Antimicrobial concentrations used for testing were selected based on the susceptible (≤4 µg/mL), intermediate (8 µg/mL), and resistant (≥16 µg/mL) breakpoints for gentamicin published by CLSI[22]. For testing, 4 µL culture samples were loaded into capillaries and subsequently into the cAST platform for automated spectral intensity measurements every 30 min over a period of 6-8 h. Positive control samples consisted of bacterial inocula in CAMHB without the addition of antimicrobials and negative control samples consisted of bacterial inocula in CAMHB with the addition of high concentrations of antimicrobials (>10×resistant breakpoint concentration).

Negative control samples were formulated in this manner to account for any interactions between non-viable/non-proliferating bacteria and resazurin.

Data Analysis

Spectral data captured by the cAST platform were imported into MATLAB (MathWorks) for analysis. Lowess regression smoothing was applied to smooth spectral data followed by algorithmic identification of local maxima in the data. Resazurin's peak absorbance is around 600 nm and this peak absorbance exhibits blueshift upon conversion of the dye into resorufin. A similar blueshift can be observed in the spectral intensity profile upon dye reduction. The difference in peak intensity (peak shift) between a test sample and negative control sample was used as a quantitative indicator of bacterial growth. Time-to-growth detection was determined using a peak shift threshold of 25 nm as non-susceptible and no-antimicrobial control samples exhibited peak shifts >30 nm upon reduction of resazurin.

Antimicrobial susceptibility verification using broth dilution

To verify concentration-dependent antimicrobial susceptibility determined using the cAST platform, broth macrodilution was concurrently conducted as a second AST method.

Using the same inoculum preparation steps outlined above, 2 mL liquid cultures with starting inoculum concentration of ~5×10[5] CFU/mL were supplemented with the same antimicrobial concentrations as the capillary samples (without resazurin) and subsequently incubated overnight in an incubator at 37° C. in ambient air. Following incubation, antimicrobial susceptibility was determined based on whether turbidity was visually observed.

Testing of Clinical Isolates

Following testing of the QC strains, the cAST platform was used to test two *E. coli* clinical isolates. Following the same protocol used to test the QC strains, the clinical isolates were tested with ten two-fold dilution gentamicin concentrations spanning 0.5 µg/mL to 256 µg/mL. Testing was conducted blind and results were subsequently compared with clinical results generated using gradient diffusion (E-test, bioMérieux).

The following results were obtained using the materials and methods described in Example 1.

Figure 3:
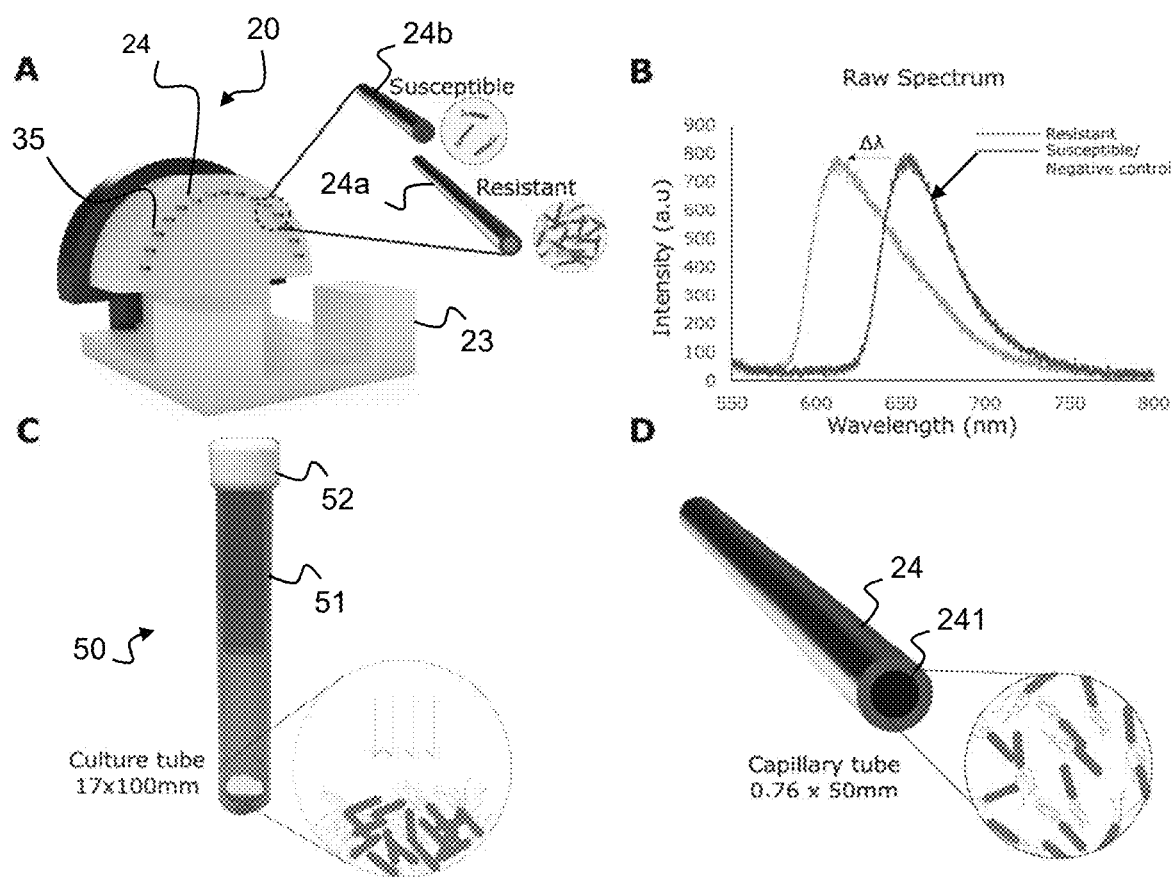
FIGS. 3A-3D. AST in capillary format.

EXAMPLE 2 cAST Platform cAST includes a combination of commercially available and customized, 3D printed parts, as generally depicted in FIG. 1 and FIG. 3. Components include a stepper motor, fiber-optic cable, portable spectrometer, light source, and 3D-printed parts designed to hold components in alignment for optical measurements. In particular, FIG. 1A shows an incubator 10 comprising a cAST device 20. The cAST device 20 may be connected to a spectrometer 40 via a fiber optic cable 30. FIG. 1B provides a view of the cAST device 20 and the fiber optic cable 30. The cAST device 20 is shown with exemplary dimensions of 8.2 cm by 10.2 cm by 7.6 cm. FIG. 1C provides an exploded view of the cAST device 20 and the fiber optic cable 30. The cAST device 20 comprises a stepper motor 21; an optical coupler 22 connected to the output shaft of the stepper motor 21 at one end, and connected to the fiber optic cable 30 at the other end; a conduit mount 23 which receives a plurality of angularly arranged conduits 24 shown as capillary tubes; and an LED holder 25. The mount 23 comprises one or a plurality of conduit holders 35. FIG. 3A is as discussed above. FIG. 3C provides a detail view of the cAST device 20, wherein the plurality of conduits 24 shown as capillary tubes received in the capillary mount 23 via a plurality of capillary holders 35 comprises a resistant culture sample 24*a* and a susceptible culture sample 24*b*. FIG. 3C shows a culture tube 50 used for storing culture samples. The culture tube 50 comprises a tubular body 51 and a cap 52. The culture tube 50 is shown with exemplary dimensions of 17 mm by 100 mm. FIG. 3D shows a capillary tube 24 as a representative conduit. The conduit 24 shown as a capillary tube comprises a lumen 241 which extends the length of the conduit 24. The conduit 24 is shown as a capillary tube with exemplary dimensions of 0.76 mm of internal diameter by 50 mm of length.

Without intending to be bound by any particular theory, it is considered that a principle of operation of cAST is as follows: light incident on one end of the conduit, illustrated using capillary tubes, passes through the sample and is then captured by the fiber-optic cable, with the capillary tube serving as an optical waveguide. The fiber-optic cable is coupled to a portable spectrometer as a light detection device that measures the spectral intensity profile of the captured light, which can be monitored for relative changes that are indicative of bacterial growth and thus antimicrobial susceptibility. By using an onboard microcontroller, measurements are automated for multiple samples at an adjustable time interval.

Again, without intending to be constrained by any particular theory, it is considered that the advantages of the cAST platform include at least the following: 1) the system enables accelerated AST, 2) the system is automated which simplifies workflow when working with multiple samples, and 3) the system enables non-contact optical interrogation of small sample volumes (<5 µL). The cylindrical form factor of a capillary tube maximizes the optical path length which facilitates optical measurements without requiring optical cavities[23] or traditional microscopy instruments for readout[16,24], components that are typically required in microfluidic systems which ultimately increase fabrication and operational complexity. In addition to these advantages, the entire cAST system has a small footprint can be built using inexpensive parts making it suitable for use in resource-limited settings.

EXAMPLE 3

Bacterial Growth in Capillary Tubes

Figure 2:
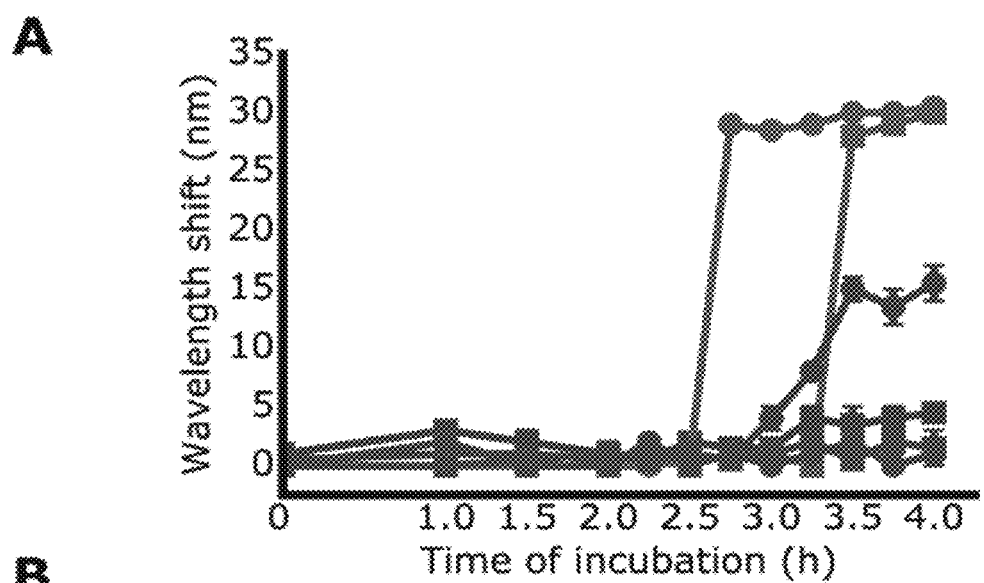
FIGS. 2A and 2B. Comparison of E. coli (ATCC 25922) growth in capillary and 384-microwell plate format.
Figure 2:
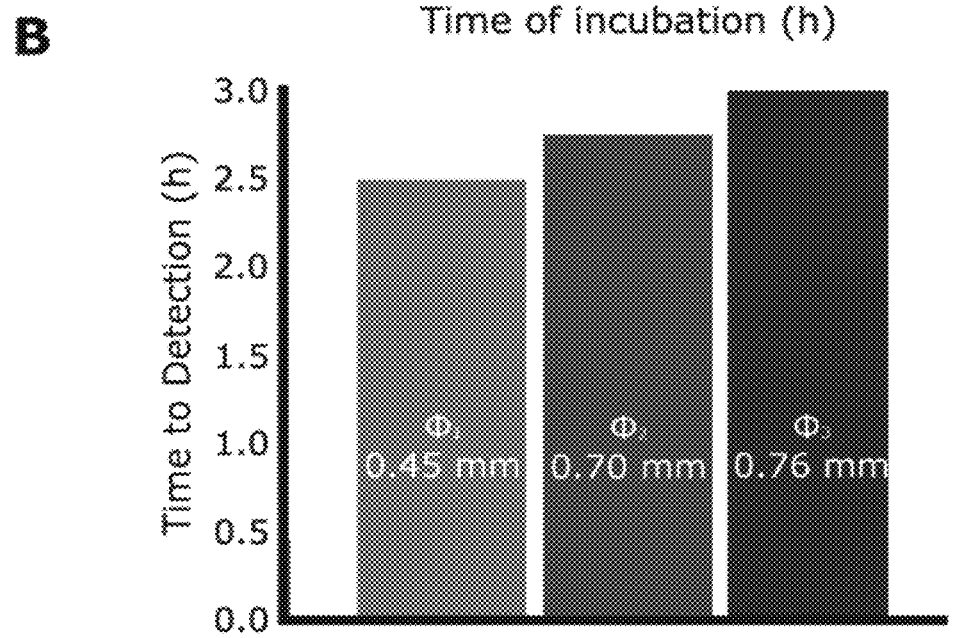

Prior to AST with the cAST platform, we compared detection of bacterial growth in capillary tube versus 384-microwell plate format using three different colorimetric indicators: phenol red, bromomethyl blue, and resazurin. By testing three colorimetric indicators, we first examined how incubation inside the capillary tube format affects bacterial growth and subsequently determine which indicator yields the fastest detection of growth. For all three colorimetric indicators, metabolically active bacteria induce color change in the media over time, which can be quantified through spectral measurements. Phenol red and bromomethyl blue are colorimetric pH indicators that change color in response to the accumulation of bacterial metabolic byproducts such as organic acids. Resazurin is a redox indicator that changes color upon reduction into resorufin by metabolically active cells[20]. Using the test organism *E. coli* (ATCC 25922) diluted to approximately $5\times10^5$ CFU/mL starting concentration, we loaded 15 µL volumes of dye-supplemented cultures into capillary tubes and a 384-microwell plate and incubated the samples at 37° C. in ambient air. Sample color change over time was quantified by measuring sample absorbance in the 350 nm-650 nm range using a microplate reader. Capillary samples were dispensed into a microplate at time of measurement to enable use of the plate reader. The difference in peak absorbance (peak shift) between a test sample and negative control sample (no bacteria) was used as a quantitative indicator of bacterial growth. As shown in FIG. 2A, incubation inside the capillary format accelerated growth detection relative to incubation inside microwell plate format and amongst the three colorimetric indicators tested, resazurin yielded the fastest detection of growth. In fact, resazurin in the capillary format yielded a time to growth detection that was 45 min faster than resazurin in the microwell format.

Using the same spectral measurement approach, we next investigated the impact of capillary tube inner diameter size on bacterial growth and time to growth detection. *E. coli* (ATCC 25922) inoculated media supplemented with resazurin, with $5\times10^5$ CFU/mL approximate starting concentration, was incubated inside capillary tubes with three different inner diameters (0.45 mm, 0.70 mm, and 0.76 mm) and incubated at 37° C. in ambient air. Sample color change over time, corresponding to bacterial growth, was quantified by measuring sample absorbance in the 350 nm-650 nm range. Because of the determined wavelength shift of resazurin reduction observed in the previous experiment (FIG. 2A), time to growth detection was determined as the time point at which a wavelength shift of greater than 25 nm was detected. As shown in FIG. 2B, an inversely proportional relationship was observed between capillary tube inner diameter and time to growth detection.

EXAMPLE 4 cAST Enabled Antimicrobial Susceptibility Testing

The cAST platform uses the described phenomenon of faster observed growth of bacteria in capillary format in the context of AST. We analyzed whether faster growth, evidenced by faster reduction of resazurin, is due to what is considered to be optimal bacteria and nutrient distribution in the capillary format. As shown in the comparison in FIGS. 3C & D, we tested to determine whether the small length scale of the capillary tube as a representative conduit leads to a uniform distribution and diffusion of bacteria within the sample matrix which likely maximizes access to nutrients and optimizes growth.

As shown in FIG. 3A, cAST enabled susceptibility testing is based on the principle that bacterial inhibition by antimicrobials will limit the reduction of resazurin into resorufin. On the other hand, non-susceptible/resistant bacteria will proliferate and reduce resazurin into resorufin, thereby inducing significant changes in the color of the sample media over time. Instead of a spectrophotometer, a portable spectrometer was used to monitor color change due to its smaller footprint and the ability to make measurements inside the incubator in real-time without interrupting sample incubation. The spectral intensity profile change corresponding to the reduction of resazurin is shown in FIG. 3B.

EXAMPLE 5

AST of Clinically Relevant Organisms

Figure 4:
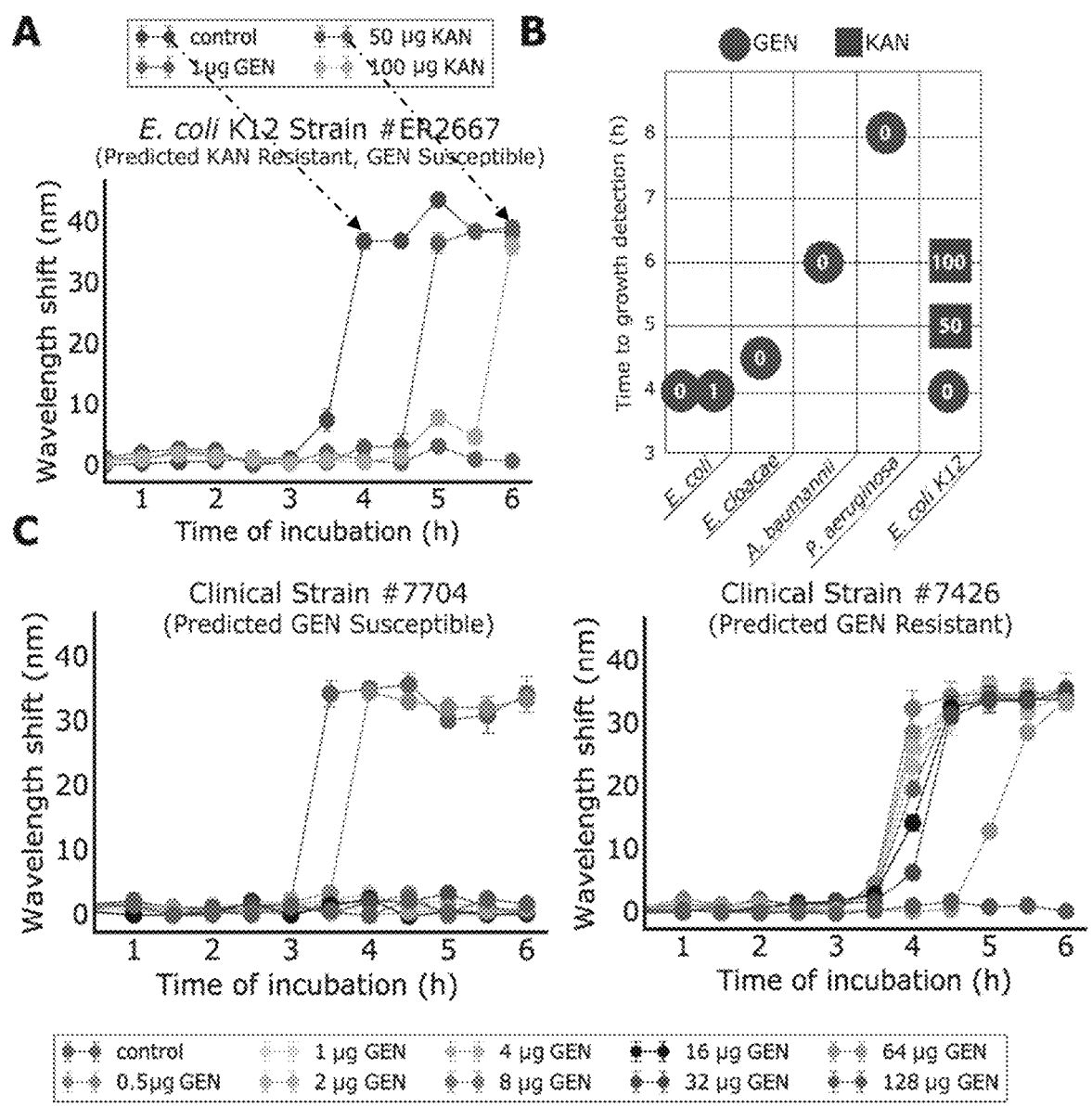
FIGS. 4A-4C. Multi-organism AST data from cAST platform.
Figure 5:
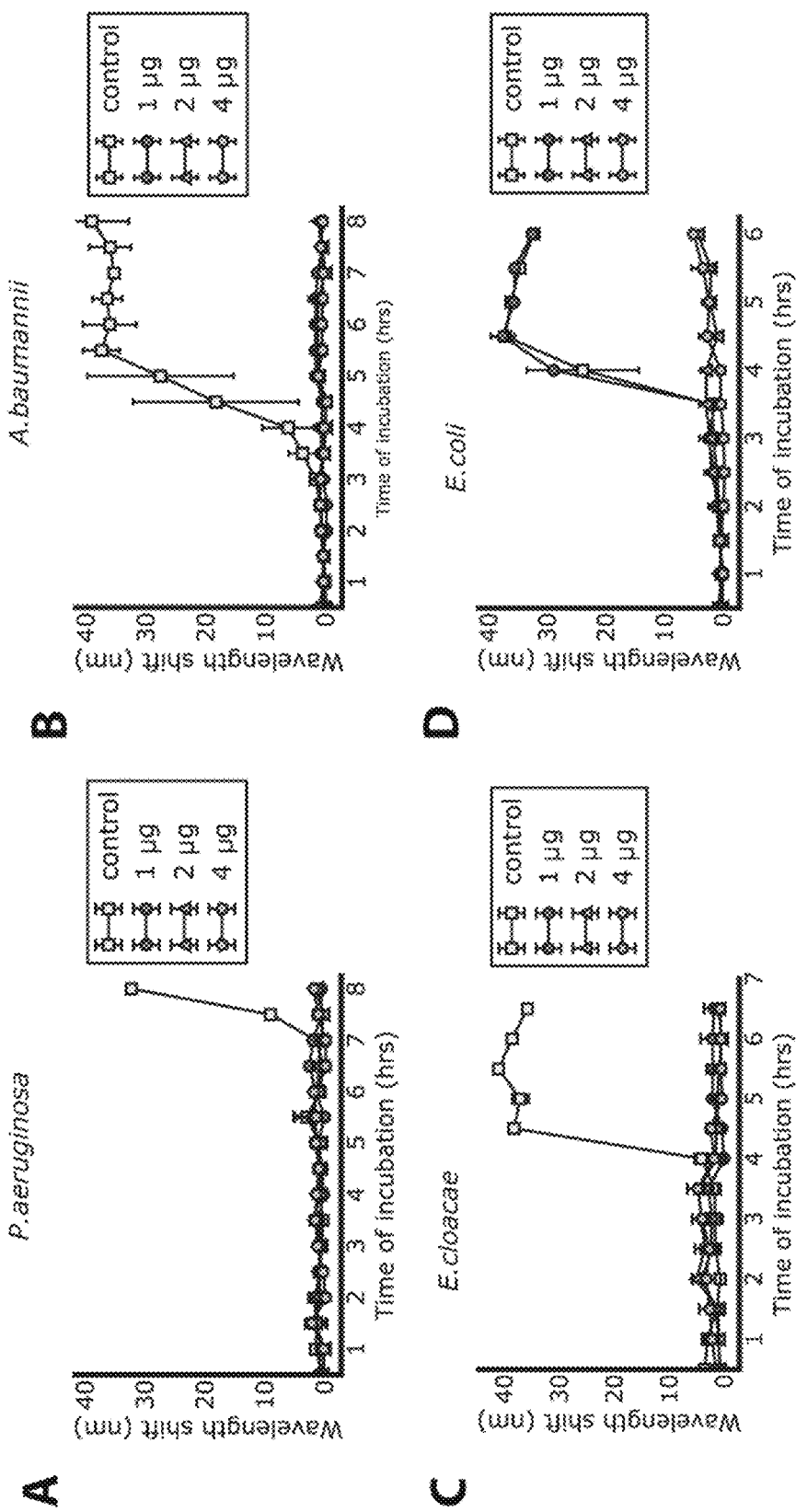
FIGS. 5A-5D. Individual cAST data for tested organisms (FIGS. 5A-5D). Bacterial strains were tested for gentamicin susceptibility.

The cAST platform was initially used to test five different QC microorganisms: *E. coli* ATCC 25922, *E. cloacae* ATCC 13047, *A. baumannii* ATCC BAA-747, *P. aeruginosa* ATCC 27853, and *E. coli* K12 ER2267 (kanamycin resistant). These bacterial species are among the prominent causes of hospital-acquired infections and are frequently AMR[25]. We tested each organism's susceptibility to the aminoglycoside gentamicin as this antimicrobial is classified by the Clinical and Laboratory Standards Institute (CLSI) as a Group A (appropriate for inclusion in a primary AST panel) antimicrobial agent against all five of the selected organisms[22]. The antimicrobial concentrations we tested (1, 2, 4, and 50 µg/mL) were selected taking into consideration the susceptible and resistant breakpoint concentrations published by CLSI. The *E. coli* K12 (kanamycin resistant) strain was tested at kanamycin concentrations of 50 and 100 µg/mL (FIG. 4A). For each organism, we collected 6-8 h of data using the cAST platform and AST results are summarized in FIG. 4B. Individual data for each organism can be found in FIG. 5. Due to resazurin's high spectral change upon reduction, the time point at which growth was detected can be determined through thresholding spectral wavelength shift data. cAST enabled AST results were verified against broth macrodilution, which showed unanimous agreement but required longer incubation.

Following testing of the five QC strains, the cAST platform was used to test two de-identified *E. coli* clinical isolates. The clinical isolates were tested with ten two-fold serial-diluted gentamicin concentrations ranging from 0.5 µg/mL to 256 µg/mL. Isolates were tested without prior knowledge of antimicrobial susceptibility profiles, and cAST results (FIG. 4C) were verified to be in categorical agreement with overnight clinical gradient diffusion results. Clinical strain 7704 tested susceptible to gentamicin with predicted MICs of 1 µg/mL (cAST at 6 h) and 1.5 µg/mL (gradient diffusion overnight). Clinical strain 7426 tested resistant to gentamicin with predicted MICs of 128 µg/mL (cAST at 6 h) and ≥256 µg/mL (gradient diffusion overnight).

In view of the foregoing description and examples, the following description is pertinent. It is estimated that for patients with septic shock, every hour that goes by without antibiotic administration results in a 7.6% drop in survival rate[26]. In time sensitive situations, rapid AST techniques are crucial for expediting the administration of effective therapy. This disclosure provides a novel, rapid AST technique based on optical interrogation of organisms incubated inside a capillary tube format, which was empirically determined to accelerate time to growth detection and readout. We were able to demonstrate off-device that incubation in the capillary format yielded an approximately 25% faster readout compared to incubation in the microwell format, which is required for absorbance measurements of small sample volumes. We demonstrated development of the cAST platform, a robust device setup that includes 3D-printed and commercially available components to enable automated optical measurements of samples housed in capillary format. With the use of a resazurin redox indicator, we were able to demonstrate reliable AST results, for five QC strains and two clinical isolates within 4-8 h. It is considered that the ease of the setup, ease of operation, and small footprint make cAST a superior platform for use in resource-limited and translational settings than has been previously available.

Without intending to be constrained by theory, it is considered that the presently provided cAST system offers several advantages relative to other AST methods. First, the low sample volume requirement (<5 µL) limits reagent consumption and is conducive to minimizing the number of pre-AST incubation steps needed to scale up organism concentration. For comparison, AST in 96-well and 384-well plate require sample volumes that are of an order of magnitude higher for absorbance-based readout. Secondly, the platform may be configured to use commercially available capillary tubes, which are reusable following sterilization and are of lower fabrication and operational complexity compared to small volume sample-holding consumables used in microfluidic systems[15-18]. Third, the small footprint and portability of the platform makes it amenable for use in point-of-care settings.

An aspect of the disclosure relates to the discovery that bacterial incubation in the described capillary form factor appears to enhance the growth rate, as evidenced by faster reduction of resazurin relative to bacterial incubation in microwells. It is considered, again without intending to be bound by any particular interpretation, that this phenomenon is due to two reasons: 1) capillary forces within the tube induce a uniform distribution of bacteria and nutrients which optimize growth or 2) bacterial confinement within small diameter capillary tubes facilitates nutrient-seeking chemotaxis behavior that promotes growth. We observed an inverse correlation we observed between tube inner diameter and time to growth detection. Smaller inner diameter tubes further accelerated growth, possibly as a result of greater internal capillary forces. In the context of optical measurements, however, decreasing the tube inner diameter comes at the cost of reduced signal output. For this reason, most of the results described in the Examples were conducted using tubes with 0.76 mm inner diameter, which without intending to be bound by any particular theory, are considered to provide an optimal balance between accelerated growth and optical signal intensity.

The disclosure includes further improvements to the cAST platform. For example, antimicrobials and resazurin can be lyophilized directly inside capillary tubes, thereby simplifying the workflow and reducing the number of manual pipetting/dilution steps needed. Through this approach, tubes can be pre-loaded with different antimicrobials at varying concentrations and all that is needed to initiate testing is rehydration of the lyophilized components with inoculated culture media. A detachable sample holder with a honeycomb-like architecture or any suitable alternative can additionally be provided to increase the number of samples that can be tested in parallel, thereby increasing multiplexing potential. As the spectrometer is the most expensive component of the current system, a less expensive system can be provided by replacing the spectrometer with a photodiode and optical filter set at the appropriate wavelength to detect reduction of resazurin. The addition of internal heating capabilities to the system, which is included in the present disclosure, will enable incubator-free AST, further improving portability and decreasing the infrastructure required for AST. The reduction of resazurin into resorufin induces both fluorescent and colorimetric changes in the culture media. The addition of fluorescence detection to the cAST platform can increase the sensitivity of growth detection. The disclosure includes testing a larger combination of antimicrobials and clinically relevant organisms to assess the broader clinical impact. It is expected the cAST platform may be adapted to accommodate organisms with long generation times (e.g., *Mycobacterium tuberculosis*) to avoid incorrect AST results following a relatively short incubation period.

Thus, in one non-limiting aspect, the disclosure provides a capillary-based platform for rapid phenotypic AST. The platform is designed to take advantage of the phenomenon that bacterial incubation inside capillary tubes enhances growth, which in turn can be leveraged for faster AST. The disclosure demonstrates that the presently provided system was able to detect bacterial growth and determine antimicrobial susceptibility for several clinically relevant organisms within 4-8 h of incubation. The cAST platform is an accessible alternative to conventional AST methods and is well-suited for use in resource-limited settings.

The following reference listing is not an indication that any reference or combination of references is material to patentability:

(1) Ventola, C. L. The Antibiotic Resistance Crisis: Part 1: Causes and Threats. *P & T: a peer-reviewed journal for formulary management* 2015, 40 (4), 277-283.

(2) CDC. *Antibiotic Resistance Threats in the United States, 2013*; 2013. https://doi.org/CS239559-B.

(3) Ventola, C. L. The Antibiotic Resistance Crisis: Part 2: Management Strategies and New Agents. *P & T: a peer-reviewed journal for formulary management* 2015, 40 (5), 344-352.

(4) Jorgensen, J. H.; Ferraro, M. J.; Jorgensen, J. H.; Ferraro, M. J. Antimicrobial Susceptibility Testing: A Review of General Principles and Contemporary Practices. *Clinical Infectious Diseases* 2009, 49 (11), 1749-1755. https://doi.org/10.1086/647952.

(5) Balouiri, M.; Sadiki, M.; Ibnsouda, S. K. Methods for in Vitro Evaluating Antimicrobial Activity: A Review. *Journal of Pharmaceutical Analysis* 2016, 6 (2), 71-79. https://doi.org/10.1016/j.jpha.2015.11.005.

(6) Kuper, K. M.; Boles, D. M.; Mohr, J. F.; Wanger, A. Antimicrobial Susceptibility Testing: A Primer for Clinicians. *Pharmacotherapy* 2009, 29 (11), 1326-1343. https://doi.org/10.1592/phco.29.11.1326.

(7) Zilberberg, M. D.; Shorr, A. F.; Micek, S. T.; Vazquez-Guillamet, C.; Kollef, M. H. Multi-Drug Resistance, Inappropriate Initial Antibiotic Therapy and Mortality in Gram-Negative Severe Sepsis and Septic Shock: A Retrospective Cohort Study. *Critical Care* 2014, 18 (6). https://doi.org/10.1186/s13054-014-0596-8.

(8) Garnacho-Montero, J.; Gutiérrez-Pizarraya, A.; Escoresca-Ortega, A.; Fernández-Delgado, E.; López-Sánchez, J. M. Adequate Antibiotic Therapy Prior to ICU Admission in Patients with Severe Sepsis and Septic Shock Reduces Hospital Mortality. *Critical Care* 2015, 19 (1). https://doi.org/10.1186/s13054-015-1000-z.

(9) van Belkum, A.; Dunne, W. M.; Jr. Next-Generation Antimicrobial Susceptibility Testing. *Journal of clinical microbiology* 2013, 51 (7), 2018-2024. https://doi.org/10.1128/JCM.00313-13.

(10) Banerjee, R.; Teng, C. B.; Cunningham, S. A.; Ihde, S. M.; Steckelberg, J. M.; Moriarty, J. P.; Shah, N. D.; Mandrekar, J. N.; Patel, R. Randomized Trial of Rapid Multiplex Polymerase Chain Reaction-Based Blood Culture Identification and Susceptibility Testing. *Clinical Infectious Diseases* 2015, 61 (7), 1071-1080. https://doi.org/10.1093/cid/civ447.

(11) Choi, J.; Yoo, J.; Lee, M.; Kim, E.-G.; Lee, J. S.; Lee, S.; Joo, S.; Song, S. H.; Kim, E.-C.; Lee, J. C.; et al. A Rapid Antimicrobial Susceptibility Test Based on Single-Cell Morphological Analysis. *Science translational medicine* 2014, 6 (267), 267ra174. https://doi.org/10.1126/scitranslmed.3009650.

(12) Yu, H.; Jing, W.; Iriya, R.; Yang, Y.; Syal, K.; Mo, M.; Grys, T. E.; Haydel, S. E.; Wang, S.; Tao, N. Phenotypic Antimicrobial Susceptibility Testing with Deep Learning Video Microscopy. *Analytical Chemistry* 2018, 90 (10), 6314-6322. https://doi.org/10.1021/acs.analchem.8b01128.

(13) Nordmann, P.; Poirel, L.; Dortet, L. Rapid Detection of Carbapenemase-Producing Enterobacteriaceae. *Emerging infectious diseases* 2012, 18 (9), 1503-1507. https://doi.org/10.3201/eid1809.120355.

(14) Pires, J.; Novais, A.; Peixe, L. Blue-Carba, an Easy Biochemical Test for Detection of Diverse Carbapenemase Producers Directly from Bacterial Cultures. *Journal of clinical microbiology* 2013, 51 (12), 4281-4283. https://doi.org/10.1128/JCM.01634-13.

(15) Cira, N. J.; Ho, J. Y.; Dueck, M. E.; Weibel, D. B. A Self-Loading Microfluidic Device for Determining the Minimum Inhibitory Concentration of Antibiotics. *Lab on a chip* 2012, 12 (6), 1052-1059. https://doi.org/10.1039/c21c20887c.

(16) Avesar, J.; Rosenfeld, D.; Truman-Rosentsvit, M.; Ben-Arye, T.; Geffen, Y.; Bercovici, M.; Levenberg, S. Rapid Phenotypic Antimicrobial Susceptibility Testing Using Nanoliter Arrays. *Proceedings of the National Academy of Sciences of the United States of America* 2017, 114 (29), E5787-E5795. https://doi.org/10.1073/pnas.1703736114.

(17) Tang, Y.; Zhen, L.; Liu, J.; Wu, J. Rapid Antibiotic Susceptibility Testing in a Microfluidic PH Sensor. *Analytical Chemistry* 2013, 85 (5), 2787-2794. https://doi.org/10.1021/ac303282j.

(18) Chen, C. H.; Lu, Y.; Sin, M. L. Y.; Mach, K. E.; Zhang, D. D.; Gau, V.; Liao, J. C.; Wong, P. K. Antimicrobial Susceptibility Testing Using High Surface-to-Volume Ratio Microchannels. *Analytical Chemistry* 2010, 82 (3), 1012-1019. https://doi.org/10.1021/ac9022764.

(19) Doern, C. D. The Slow March toward Rapid Phenotypic Antimicrobial Susceptibility Testing: Are We There Yet? *Journal of clinical microbiology* 2018, 56 (4), e01999-17. https://doi.org/10.1128/JCM.01999-17.

(20) Guerin; Mondido; McClenn; Peasley. Application of Resazurin for Estimating Abundance of Contaminant-Degrading Micro-Organisms. *Letters in Applied Microbiology* 2001, 32 (5), 340-345. https://doi.org/10.1046/j.1472-765X.2001.00916.x.

(21) Wiegand, I.; Hilpert, K.; Hancock, R. E. W. Agar and Broth Dilution Methods to Determine the Minimal Inhibitory Concentration (MIC) of Antimicrobial Substances. *Nature Protocols* 2008, 3 (2), 163-175. https://doi.org/10.1038/nprot.2007.521.

(22) Clinical and Laboratory Standards Institute. *M100 Performance Standards for Antimicrobial Susceptibility Testing;* 2019.

(23) Rushworth, C. M.; Davies, J.; Cabral, J. T.; Dolan, P. R.; Smith, J. M.; Vallance, C. Cavity-Enhanced Optical Methods for Online Microfluidic Analysis. *Chemical Physics Letters* 2012, 554, 1-14. https://doi.org/10.1016/J.CPLETT.2012.10.009.

(24) Magnusson, E. B.; Halldorsson, S.; Fleming, R. M. T.; Leosson, K. Real-Time Optical PH Measurement in a Standard Microfluidic Cell Culture System. *Biomedical Optics Express* 2013, 4 (9), 1749. https://doi.org/10.1364/BOE.4.001749.

(25) Peleg, A. Y.; Hooper, D. C. Hospital-Acquired Infections Due to Gram-Negative Bacteria. *New England Journal of Medicine* 2010, 362 (19), 1804-1813. https://doi.org/10.1056/NEJMra0904124.

(26) Ferrer, R.; Martin-Loeches, I.; Phillips, G.; Osborn, T. M.; Townsend, S.; Dellinger, R. P.; Artigas, A.; Schorr, C.; Levy, M. M. Empiric Antibiotic Treatment Reduces Mortality in Severe Sepsis and Septic Shock from the First Hour: Results from a Guideline-Based Performance Improvement Program. *Critical care medicine* 2014, 42 (8), 1749-1755. https://doi.org/10.1097/CCM.0000000000000330.

(27) Berg, H. C.; Turner, L. Chemotaxis of Bacteria in Glass Capillary Arrays. Escherichia Coli, Motility, Microchannel Plate, and Light Scattering. *Biophysical journal* 1990, 58 (4), 919-930. https://doi.org/10.1016/50006-3495(90)82436-X.

(28) Ping, L.; Wasnik, V.; Emberly, E. Bacterial Motion in Narrow Capillaries. *FEMS Microbiology Ecology* 2015, 91 (2), 1-7. https://doi.org/10.1093/femsec/fiu020.

Although the present disclosure has been described using specific embodiments and examples, routine modifications will be apparent to those skilled in the art and such modifications are intended to be within the scope of the disclosure and the claims.

What is claimed is:

1. A method for analyzing bacteria for antimicrobial susceptibility, the method comprising:
   i) providing a system comprising:
      a) at least one mount defining a plurality of holders, each holder configured to receive a conduit extending along a longitudinal axis by a length between a first end and a second end, the conduit defining a lumen configured to hold a liquid sample;
      b) at least one light source configured to output light to a first end of a conduit disposed in each of the plurality of holders; and
      c) at least one light detection device configured to receive light emitted from the second end of a conduit disposed in each of the plurality of holders following transmission of the light through a liquid sample borne in the lumen and to output a signal relating to a value of one or more components of the light emitted from the second end of the conduit,
   ii) selecting a conduit comprising a lumen from a plurality of conduits;
   iii) introducing a liquid sample into the lumen of the conduit, the liquid sample comprising bacteria, a dye, and an antimicrobial agent;
   iv) disposing the conduit in a selected one of the plurality of holders;
   v) incubating the liquid sample in the lumen of the conduit for a predetermined period of time between about 2 hours and about 16 hours;

vi) following the incubating of the liquid sample for the predetermined period of time, transmitting light from the at least one light source sequentially through the first end of the conduit, the liquid sample in the lumen, and the second end of the conduit to the at least one light detection device;

vii) detecting the light emitted from the second end of the conduit using the at least one light detection device and outputting, from the at least one light detection device, a signal relating to a value of one or more components of the light emitted from the second end of the conduit; and viii) determining a difference between the value of the one or more components of the light emitted from the second end of the conduit to a control value, the difference relating to a sensitivity of the bacteria in the liquid sample to the antimicrobial agent.

2. The method of claim 1, wherein the introducing the liquid sample into the lumen of the conduit comprises disposing the first end or the second end of the conduit in contact with the liquid sample to draw the liquid sample into the lumen via capillary action.

3. The method of claim 1, comprising performing the acts of each of ii)-viii) for each of the plurality of conduits to analyze a plurality of liquid samples, wherein each liquid sample in the plurality of liquid samples is disposed within a lumen of a respective one of the plurality of conduits.

4. The method of claim 3, wherein each liquid sample of the plurality of liquid samples contains a different dye, a different bacteria and/or a different antimicrobial agent.

5. The method of claim 4, wherein each liquid sample of the plurality of liquid samples contains a dye.

6. The method of claim 5, wherein the dye comprises resazurin.

7. The method of claim 3, wherein each of the liquid samples is equal to or less than 5 µL in volume.

8. The method of claim 3, wherein each of the plurality of liquid samples is equal to or less than 5 µL in volume, and wherein the predetermined period of time for incubating the liquid sample in the respective lumen of each the plurality of conduits is between about 4 hours and about 8 hours.

9. The method of claim 3, wherein the plurality of conduits are between about 5 mm and about 100 mm in length and wherein each lumen has a diameter of between about 50 µm and 2 mm.

10. The method of claim 3, further comprising, following the introducing of the liquid sample into the lumen of each of the plurality of conduits, disposing a first removable cap to occlude the first open end of a respective one of the plurality of conduits and disposing a second removable cap to occlude the second open end of the respective one of the plurality of conduits, wherein the first removable cap and the second removable cap are transparent at least in portions disposed adjacent to an interior volume of the lumen.

11. The method of claim 3, further comprising moving the at least one light source and the at least one light detection device relative to the at least one mount, or moving the at least one mount relative to the at least one light source and the at least one light detection device, via a motor operatively connected to the at least one light source and the at least one light detection device or to the at least one mount, to selectively position the at least one light source and the at least one light detection device adjacent to a selected one of the plurality of conduits.

12. The method of claim 11, wherein the at least one light source is a single light source.

13. The method of claim 11, wherein the at least one light detection device comprises a single spectrometer.

14. The method of claim 1, wherein the plurality of conduits are opaque.

15. The method of claim 1, wherein the plurality of conduits comprise metal capillary tubes.

16. The method of claim 1, wherein the predetermined period of time for incubating the liquid sample in the lumen of the conduit is between about 4 hours and about 8 hours.

17. The method of claim 1, further comprising, following the introducing of the liquid sample into the lumen of the conduit, disposing a first removable cap to occlude the first open end of the conduit and disposing a second removable cap to occlude the second open end of the conduit, wherein the first removable cap and the second removable cap are transparent at least in portions disposed adjacent to an interior volume of the lumen.

18. The method of claim 1, wherein the at least one light source comprises one or more light emitting diodes and/or wherein the at least one light detection device comprises a spectrometer.

19. The method of claim 1, wherein the only optical element between the second end of the conduit disposed in the selected holder and the at least one light detection device is a light pipe configured to transmit an entire light spectrum emitted from the second end of the conduit to the at least one light detection device.

20. The method of claim 1, wherein detecting the light emitted from the second end of the conduit using the at least one light detection device comprises analyzing the light to determine colorimetric and fluorescence signal changes.

* * * * *